US012478547B2

(12) United States Patent
Kim et al.

(10) Patent No.: US 12,478,547 B2
(45) Date of Patent: Nov. 25, 2025

(54) WEARABLE DEVICE

(71) Applicant: LG ELECTRONICS INC., Seoul (KR)

(72) Inventors: Nayoung Kim, Seoul (KR); Dongwon Kim, Seoul (KR); Yongju Yang, Seoul (KR); Gueisam Lim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 992 days.

(21) Appl. No.: 17/626,094

(22) PCT Filed: Aug. 10, 2020

(86) PCT No.: PCT/KR2020/010557

§ 371 (c)(1),
(2) Date: Jan. 10, 2022

(87) PCT Pub. No.: WO2022/010025

PCT Pub. Date: Jan. 13, 2022

(65) Prior Publication Data

US 2023/0248610 A1 Aug. 10, 2023

(30) Foreign Application Priority Data

Jul. 10, 2020 (KR) ........................ 10-2020-0085605

(51) Int. Cl.
*A61H 23/02* (2006.01)
*A61N 7/00* (2006.01)

(52) U.S. Cl.
CPC ........... *A61H 23/0245* (2013.01); *A61N 7/00* (2013.01); *A61H 2201/165* (2013.01); *A61H 2205/022* (2013.01); *A61N 2007/0034* (2013.01)

(58) Field of Classification Search
CPC .......... A61H 23/0245; A61H 2205/022; A61H 2201/1207; A61H 23/02; A61H 2201/165;
(Continued)

(56) References Cited

U.S. PATENT DOCUMENTS 5,672,153 A * 9/1997 Lax .................... A61B 10/0275 604/22
2005/0148984 A1* 7/2005 Lindsay .............. A61F 13/5611 604/387
(Continued)

FOREIGN PATENT DOCUMENTS

JP 201506521 3/2014
KR 200332096 10/2003
(Continued)

OTHER PUBLICATIONS

KR 20130110365, English Language machine translation (Year: 2013).*
(Continued)

*Primary Examiner* — Wesley G Harris
(74) *Attorney, Agent, or Firm* — LEE, HONG, DEGERMAN, KANG & WAIMEY

(57) ABSTRACT

A wearable device according to an embodiment of the present invention includes an inner body; an ultrasonic generator attached to the inner body, an outer body attached to the ultrasonic generator, wherein the ultrasonic generator includes at least one ultrasonic vibrator, a positive electrode substrate connected to the at least one ultrasonic vibrator, and a negative electrode substrate connected to the at least one ultrasonic vibrator, wherein the at least one ultrasonic vibrator is disposed between the positive electrode substrate and the negative electrode substrate.

16 Claims, 8 Drawing Sheets

(58) Field of Classification Search
CPC .......... A61H 2201/10; A61H 2201/105; A61N 7/00; A61N 2007/0034; A61N 5/0616; A45D 2200/207; A45D 44/002; A61M 37/0092; A61M 2037/0007; A61M 35/10
See application file for complete search history.

(56) References Cited

U.S. PATENT DOCUMENTS

| | | | | |
|---|---|---|---|---|
| 2011/0215673 | A1* | 9/2011 | Lan | A61N 7/00<br>310/306 |
| 2014/0121588 | A1* | 5/2014 | Ko | B06B 1/0603<br>604/22 |
| 2014/0276248 | A1* | 9/2014 | Hall | A61N 1/30<br>604/20 |
| 2014/0364794 | A1* | 12/2014 | Jordan | A61N 1/303<br>604/20 |
| 2015/0272906 | A1* | 10/2015 | Jordan | A61M 37/00<br>604/20 |

FOREIGN PATENT DOCUMENTS

| | | | | | |
|---|---|---|---|---|---|
| KR | 20090003453 | U | * | 4/2009 | A61H 23/02 |
| KR | 2020090003453 | | | 4/2009 | |
| KR | 20130097458 | A | * | 9/2013 | A61H 23/00 |
| KR | 1020130097458 | | | 9/2013 | |
| KR | 20130110365 | A | * | 10/2013 | A61N 5/06 |
| KR | 1020160037597 | | | 4/2016 | |
| KR | 20210007912 | A | * | 1/2021 | A61N 7/00 |
| WO | WO-9956829 | A1 | * | 11/1999 | A61N 7/00 |
| WO | WO-0189723 | A1 | * | 11/2001 | A61F 7/00 |
| WO | WO-2018090892 | A1 | * | 5/2018 | G06F 3/0414 |

OTHER PUBLICATIONS

KR 20130097458, English Language machine translation (Year: 2013).*

* cited by examiner

[Fig. 1]
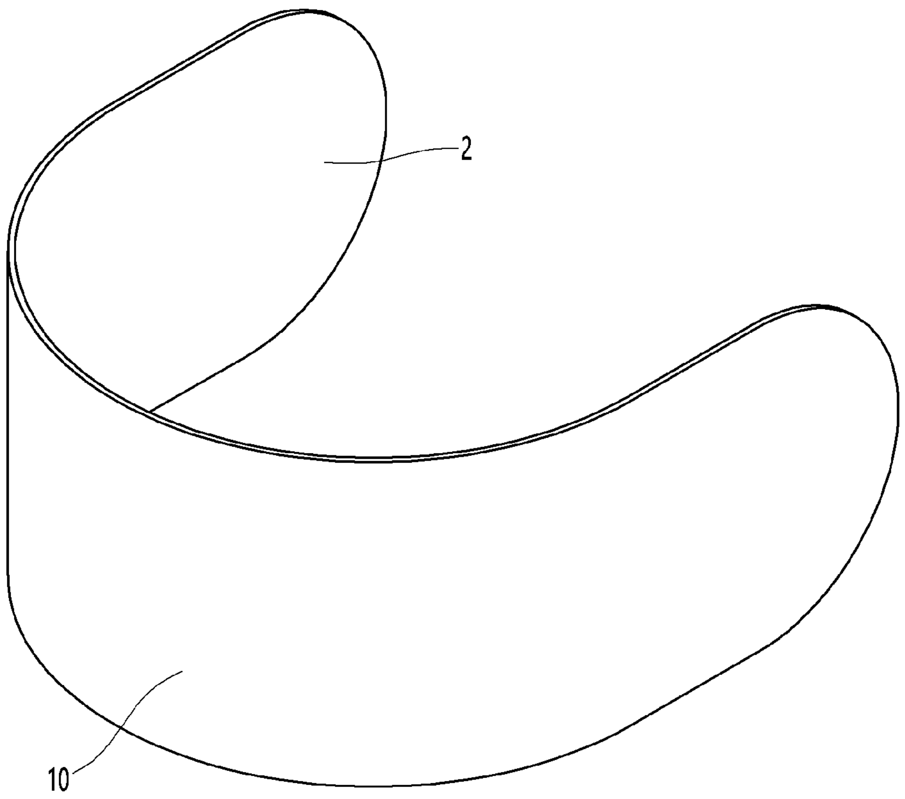

[Fig. 2]
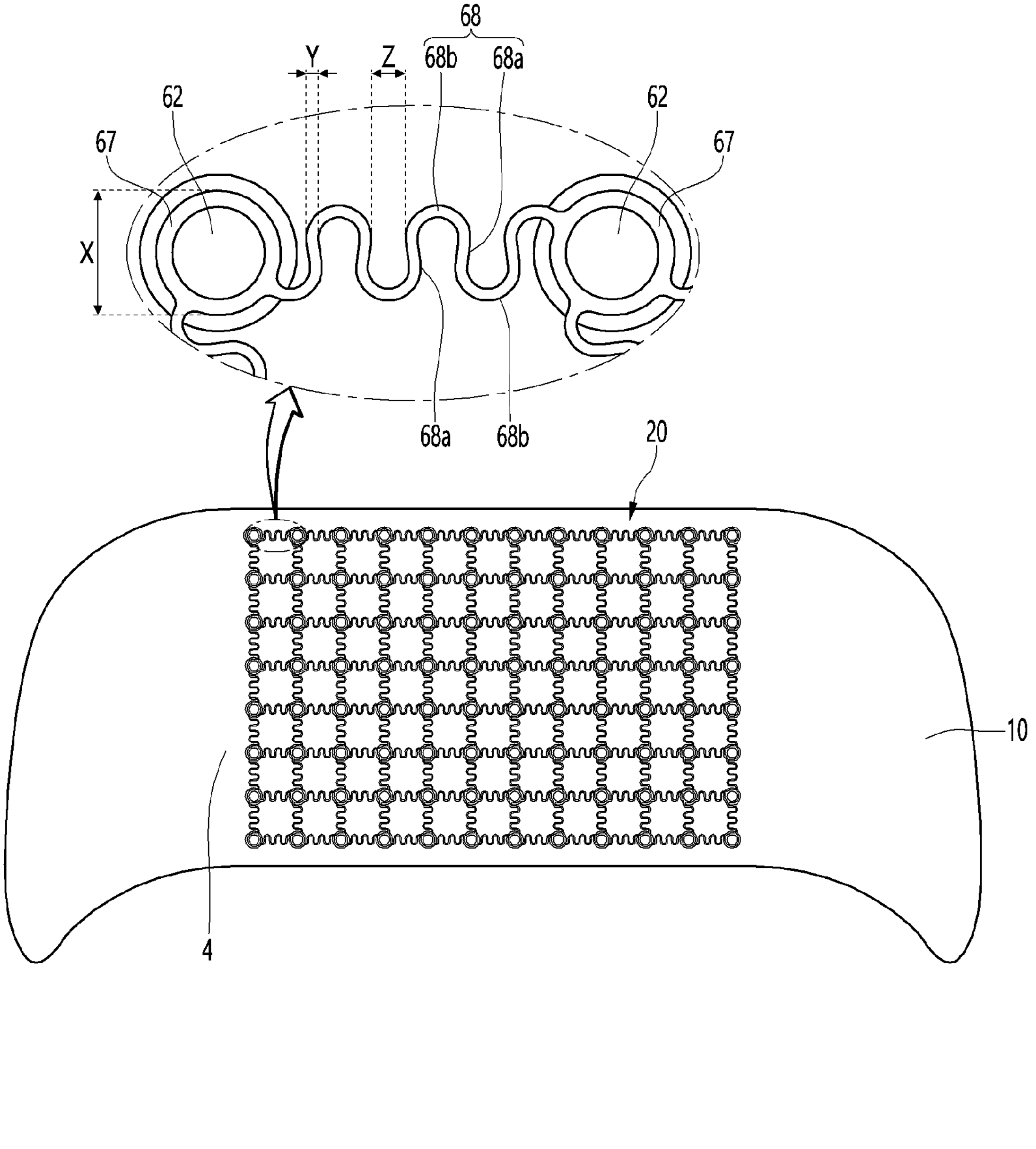

[Fig. 3]
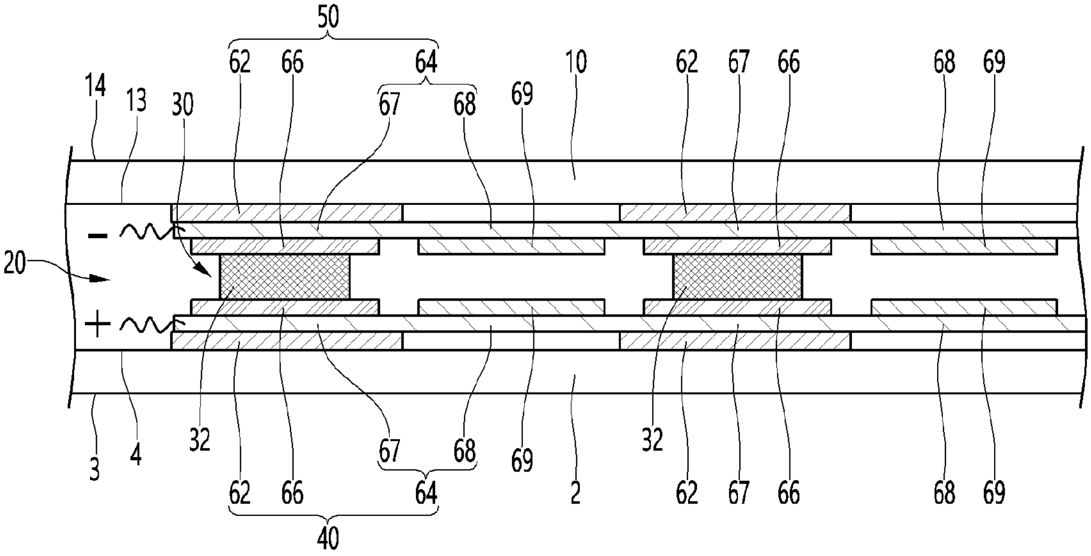

[Fig. 4]
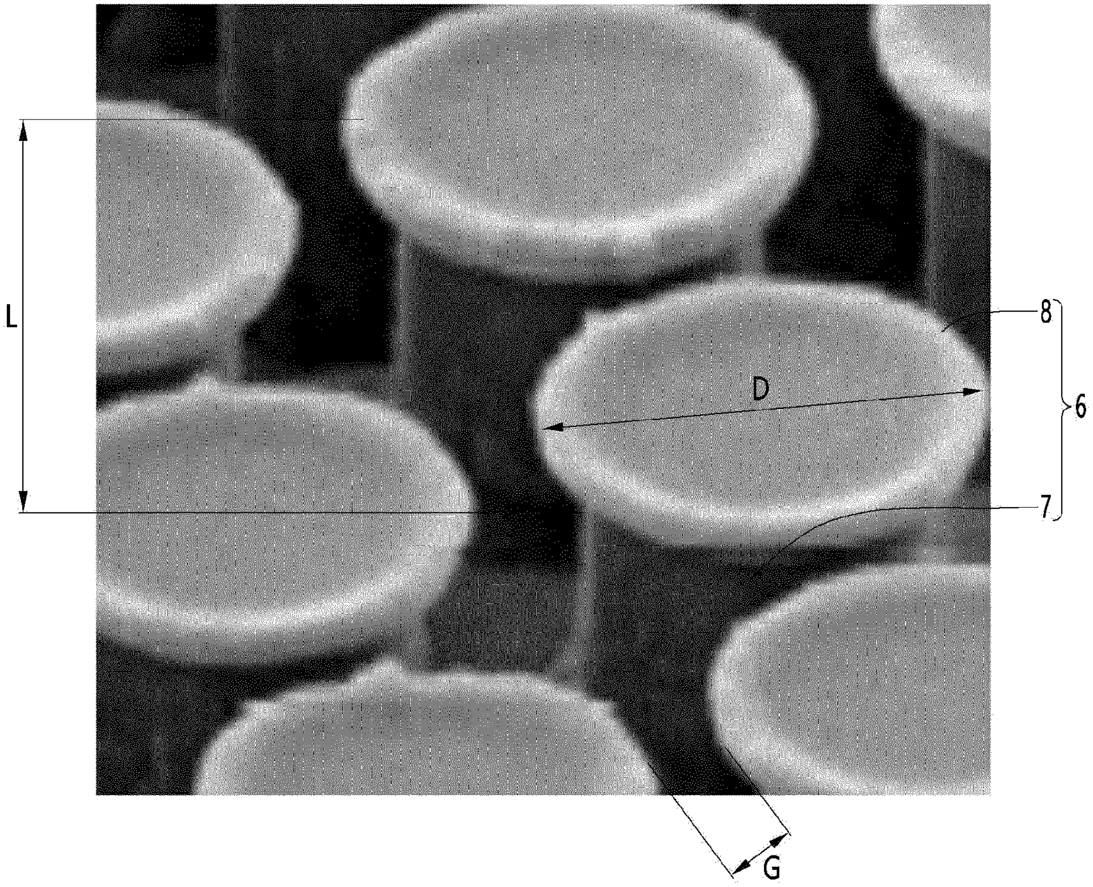

[Fig. 5]
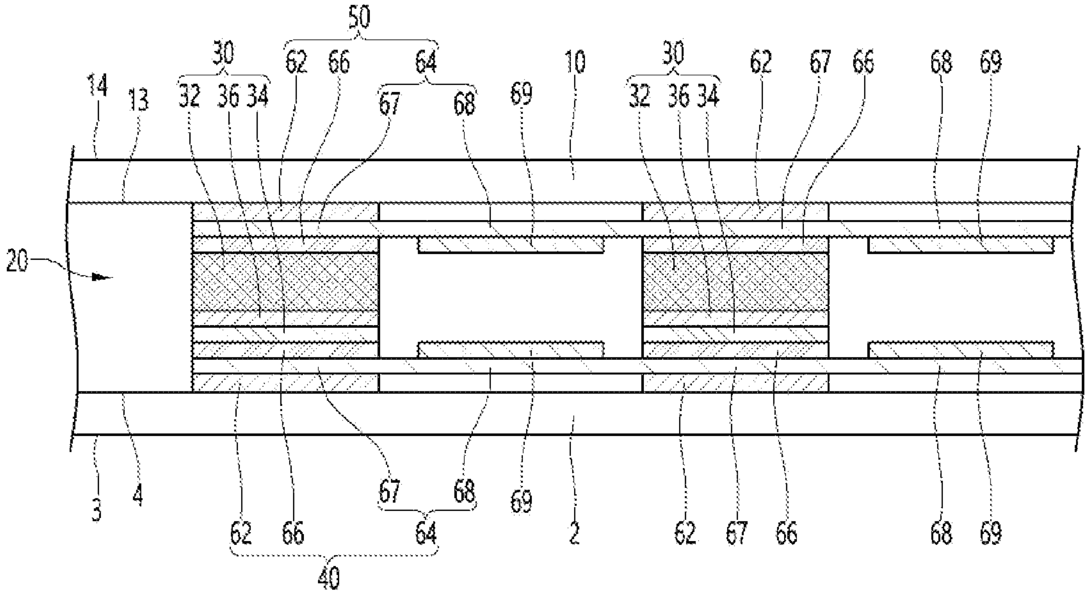
[Fig. 6]
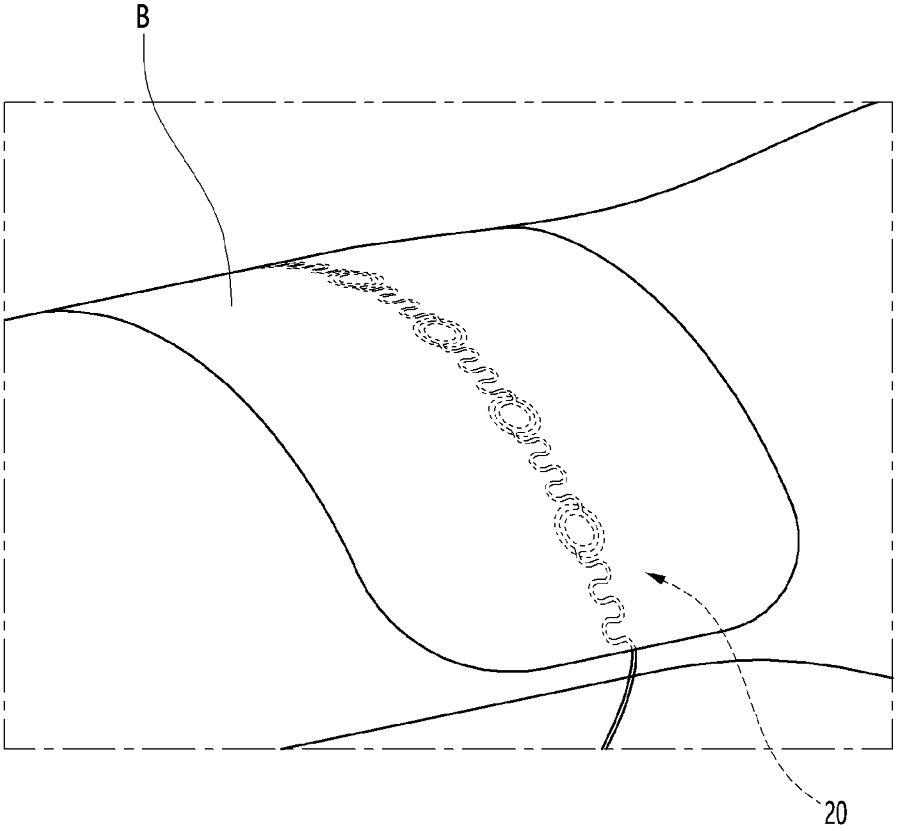

[Fig. 7]
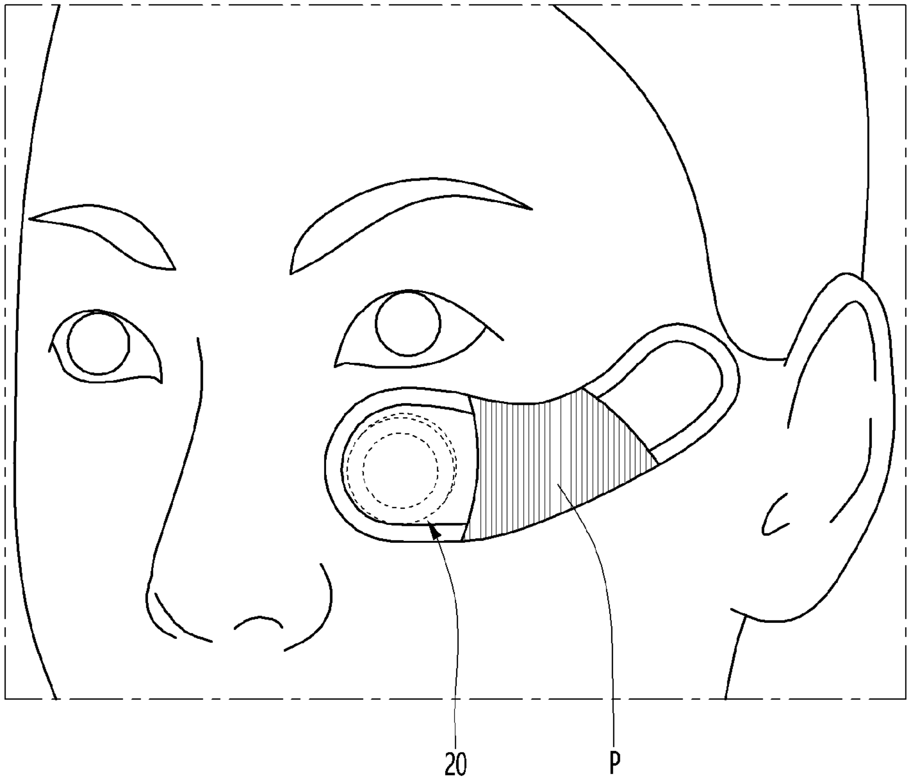

[Fig. 8]
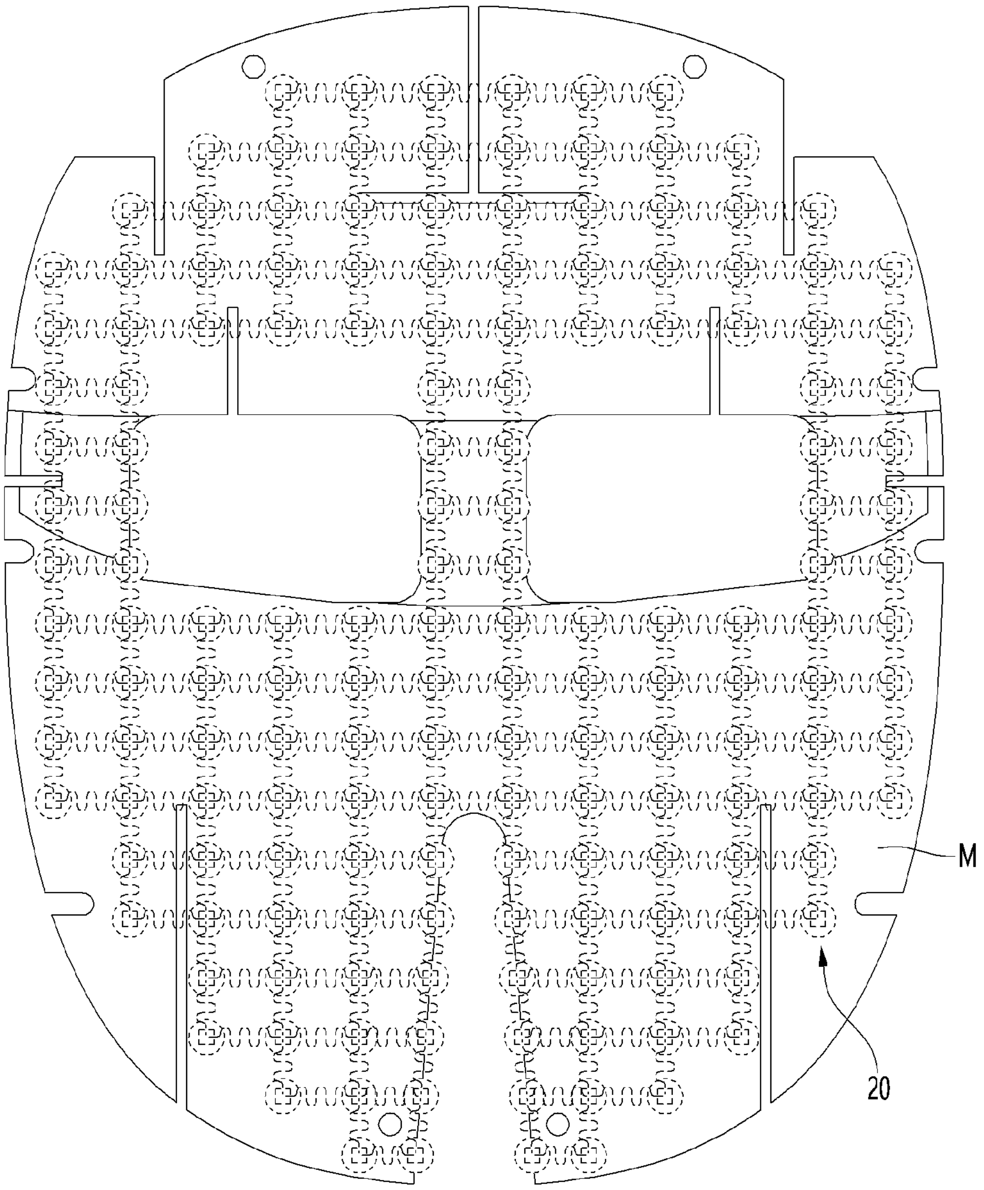

[Fig. 9]
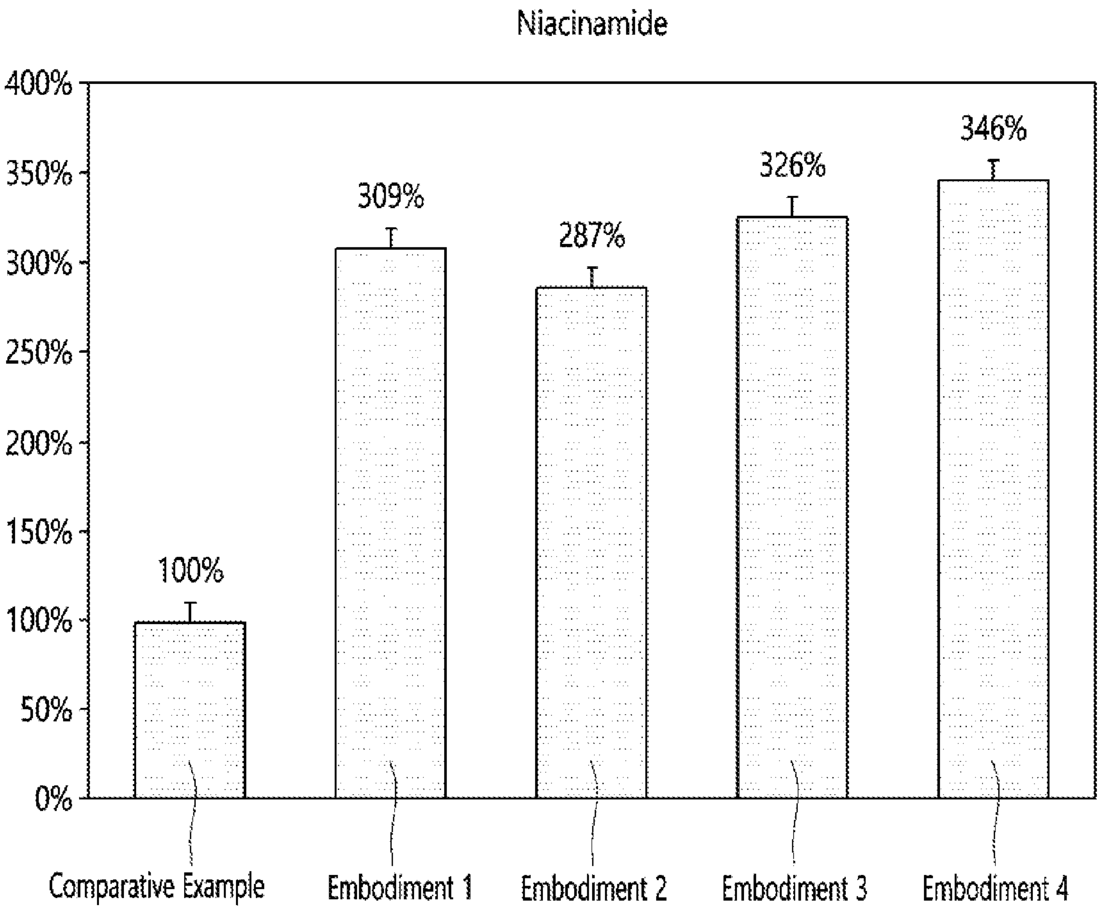

WEARABLE DEVICE

CROSS-REFERENCE TO RELATED APPLICATIONS

This application is the National Stage filing under 35 U.S.C. 371 of International Application No. PCT/KR2020/010557, filed on Aug. 10, 2020, which claims the benefit of earlier filing date and right of priority to Korean Application No. 10-2020-0085605, filed on Jul. 10, 2020, the contents of which are all hereby incorporated by reference herein in their entirety.

TECHNICAL FIELD

The present invention relates to a wearable device.

BACKGROUND ART

A wearable device is an electronic device that is used to be attached to or worn on a user's body.

Examples of the wearable device may be applied in various fields, and there is a beauty device or a medical device (or treatment device) that includes an ultrasonic vibration element to generate ultrasonic waves and transmit the ultrasonic waves to the user's skin.

An example of the ultrasonic vibration element is disclosed in Utility Model Registration No. 20-0332096 Y1 (published on Nov. 10, 2003), and includes an ultrasonic vibration ceramic for ultrasonic vibration, a conductive ultrasonic vibration and ion transfer head having a surface capable of transmitting the ultrasonic vibration and serving as one electrode during an iontophoresis function, a copper plate that transfers vibration between the vibration ceramic and the ion transfer head, and a flexible PCB serving as an insulating layer that insulates the copper plate.

DISCLOSURE OF THE INVENTION

Technical Problem

An object of the present invention is to provide a wearable device that has a simple structure and firmly adheres.

Technical Solution

A wearable device according to an embodiment of the present invention includes: an inner body; an ultrasonic generator attached to the inner body; an outer body attached to the ultrasonic generator, wherein the ultrasonic generator includes: at least one ultrasonic vibrator; a positive electrode substrate connected to the at least one ultrasonic vibrator; and a substrate connected to the at least one ultrasonic vibrator, wherein the at least one ultrasonic vibrator is disposed between the positive electrode substrate and the negative electrode substrate.

At least one of the positive electrode substrate or the negative electrode substrate includes: an insulating film; and a conductive sheet attached to the insulating film and further includes a conductive adhesive disposed between the conductive sheet and the ultrasonic vibrator.

The ultrasonic vibrator may be provided in plurality between the positive electrode substrate and the negative electrode substrate, and the plurality of ultrasonic vibrators may be spaced apart from each other.

The plurality of ultrasonic vibrators may be spaced an interval of about 5 mm or more from each other.

The conductive sheet may include a conductive sheet portion disposed between the conductive adhesive and the insulating film. The conductive sheet portion may be provided in plurality. The conductive sheet may include a bridge configured to connect a pair of conductive sheet portions of the plurality of conductive sheet portions to each other.

The bridge may be provided in plurality. Each of the plurality of bridges may have a zigzag shape.

The wearable device may further include an insulating body attached to the plurality of bridges.

An insulating body is disposed on the bridges of each of the positive electrode substrate and the negative electrode substrate, wherein the insulating body is disposed on each of surfaces facing the bridges of a different substrates facing each other.

The insulating film may be made of a PI material, the conductive sheet may be made of a copper material, and the conductive adhesive may include a conductive double-sided tape.

At least one of the inner body or the outer body may be made of silicon.

The ultrasonic vibrator may include: an oscillator; and a frequency correction member disposed between the oscillator and the positive electrode substrate.

The frequency correction member may be made of an aluminum material.

The wearable device may further include an inner adhesive member disposed between the oscillator and the frequency correction member.

The inner adhesive member may be made of a mixture of conductive epoxy and AL.

The positive electrode substrate may be attached to the inner body.

A whole or a portion of the positive electrode substrate may be disposed between the ultrasonic vibrator and the inner body.

A plurality of protrusions may protrude from an outer surface of the inner body.

Each of the plurality of protrusions may include: a pillar protruding from the inner body; and a head protruding from an end of the pillar.

Each of the plurality of protrusions may have a length of 50 μm to about 1,000 μm, and the head may have a diameter of about 50 μm to about 300 μm.

A distance between the heads may range of about 50 μm to about 1,000 μm.

Advantageous Effects

According to the embodiment of the present invention, the at least one of the positive electrode substrate or the negative electrode substrate may further include the conductive adhesive disposed between the conductive sheet and the ultrasonic vibrator so that the positive electrode substrate or the negative electrode substrate is reliably fixed to the ultrasonic vibrator.

In addition, the conductive sheet may include the plurality of conductive sheet portions and the bridge connecting the pair of conductive sheet portions of the plurality of conductive sheet portions to each other so that the inner body or the outer body is bent together with the bridge, and the inner body transmits the ultrasonic waves in the state of being in close contact with the user's body.

In addition, the plurality of protrusions may protrude from the outer surface of the inner body, and thus, the inner body may be attached and detached harmlessly to the user's body without an additional adhesive.

In addition, the wearable device may include the insulating body attached to the plurality of bridges so that the bent or curved bridge is safely used without begin disconnected.

BRIEF DESCRIPTION OF THE DRAWINGS

FIG. 1 is a view illustrating an example of a wearable device according to an embodiment of the present invention.

FIG. 2 is a front view illustrating the inside of the wearable device of FIG. 1.

FIG. 3 is a cross-sectional view illustrating an example of the wearable device according to an embodiment of the present invention.

FIG. 4 is an enlarged view of an inner protrusion according to an embodiment of the present invention.

FIG. 5 is a cross-sectional view illustrating another example of the wearable device according to an embodiment of the present invention.

FIG. 6 is a view illustrating an example in which the wearable device is a band attached to a wrist according to an embodiment of the present invention.

FIG. 7 is a view illustrating an example in which the wearable device is a patch attached to a face according to an embodiment of the present invention.

FIG. 8 is a view illustrating an example in which the wearable device is a mask according to an embodiment of the present invention.

FIG. 9 is a view illustrating performance of the wearable device according to an embodiment of the present invention.

MODE FOR CARRYING OUT THE INVENTION

Hereinafter, detailed embodiments of the present invention will be described in detail with reference to the accompanying drawings.

FIG. 1 is a view illustrating an example of a wearable device according to an embodiment of the present invention, FIG. 2 is a front view illustrating the inside of the wearable device of FIG. 1, and FIG. 3 is a cross-sectional view illustrating an example of the wearable device according to an embodiment of the present invention.

A wearable device according to this embodiment may be a body band, a waist band or a mask worn on the human body and may include a film-type flexible ultrasonic generator and thus be effective for skin care and body care.

The wearable device may include an inner body 2, an outer body 10, and an ultrasonic generator 20 disposed between the inner body 2 and the outer body 10.

The inner body 2 may be defined as a body facing a user's body when the wearable device is worn. An inner surface 3 of the inner body 2 may face the user's body, and an outer surface 4 of the inner body 2 may face an inner surface 13 of the outer body 10.

The outer body 10 may be defined as a body facing outward when the wearable device is worn. The inner surface 13 of the outer body 10 may face the outer surface 4 of the inner body 2, and the outer surface 14 of the outer body 10 may face the outside.

The outer body 10 may be attached to the ultrasonic generator 20.

Each of the inner body 2 and the outer body 10 may be made of a flexible or stretchable material. At least one of the inner body 2 or the outer body 10 may be made of silicone. The inner body 2 may be a portion that is in contact with the user's body and may be in close contact with the user's body along a curved surface.

Particularly, the inner body 2 may have a stable chemical structure and be a silicone elastomer with various properties such as heat resistance, cold resistance, electrical insulation, chemical stability, abrasion resistance, gloss, and abundant elasticity, as a non-corrosive and non-oxidizing compound.

The ultrasonic generator 20 may be attached to the inner body 2. The ultrasonic generator 20 may be attached to the outer body 10. The ultrasonic generator 20 may be accommodated between the outer surface 4 of the inner body 2 and the inner surface 13 of the outer body 10.

The ultrasonic generator 20 may be a flexible ultrasonic generator and include at least one ultrasonic vibrator 30, an positive electrode substrate 40 connected to the at least one ultrasonic vibrator 30, and a negative electrode substrate 50 connected to the at least one ultrasonic vibrator 30.

The at least one ultrasonic vibrator 30 may be disposed between the positive electrode substrate 40 and the negative electrode substrate 50.

Each of the positive electrode substrate 40 and the negative electrode substrate 50 may be a flexible substrate that is capable of being bent and curved. That is, the ultrasonic generator 20 may be a film-type ultrasonic generator.

The whole or a portion of the positive electrode substrate 40 may be disposed between the ultrasonic vibrator and the inner body 2. The positive electrode substrate 40 may be attached to the inner body 2.

The whole or a portion of the negative electrode substrate 50 may be disposed between the ultrasonic vibrator and the outer body 10. The negative electrode substrate 50 may be attached to the outer body 10.

At least one of the positive electrode substrate 40 and the negative electrode substrate 50 may include an insulating film 62, a conductive sheet 64 attached to the insulating film 62, and a conductive adhesive 66 disposed between the conductive sheet 64 and the ultrasonic vibrator 30.

The insulating film 62 may be made of a polyimide (PI) material or a PI film.

The conductive sheet 64 may be made of a copper material or may be a copper sheet (Cu sheet).

The conductive adhesive 66 may be a conductive double-sided tape.

The insulating film 62 may cover the conductive sheet 64, and the insulating film 62 of the insulating film 62 and the conductive adhesive 66 may be disposed at an opposite side of the conductive adhesive 66 with respect to the conductive sheet 64.

The conductive sheet 64 may be disposed between the insulating film 62 and the conductive adhesive 66.

The conductive adhesive 66 may electrically connect the conductive sheet 64 to the ultrasonic vibrator 30. The conductive adhesive 66 of the insulating film 62 and the conductive adhesive 66 may face the ultrasonic vibrator 30.

The conductive adhesive 66 may be an adhesive including a conductive filler. The conductive filler of the conductive adhesive 66 may be an electrically conductive metal such as silver (Ag), copper (Cu), aluminum (AL), iron (Fe), or the like.

A conductive silicone adhesive filled with graphite, a two-component epoxy adhesive composed of a silver-filled resin and a curing material, a one-component epoxy adhesive that is a silver-filled thermosetting adhesive, a silver (Ag)-filled polyurethane adhesive, or the like may be applied for the conductive adhesive 66.

Each of the positive electrode substrate 40 and the negative electrode substrate 50 may include the insulating film 62, the conductive sheet 64, and the conductive adhesive 66.

The insulating film 62 of the positive electrode substrate 40 may be in contact with the outer surface 4 of the inner body 2, and the insulating film 62 of the negative electrode substrate 50 may be in contact with the inner surface 13 of the outer body 10.

As the wearable device configured as described above approaches the user's body, the outer body 10, the insulating film 62, the conductive sheet 64, the conductive adhesive 66, the ultrasonic vibrator 30, the conductive adhesive 66, the conductive sheet 64, the insulating film 62, and the inner body 2 may be sequentially disposed.

The plurality of ultrasonic vibrators 30 may be spaced apart from each other. The plurality of ultrasonic vibrators may be spaced an interval of about 5 mm or more from each other.

The ultrasonic vibrator 30 may include an oscillator 32 disposed between the positive electrode substrate 40 and the negative electrode substrate 50.

An example of the oscillator 32 may be an ultrasonic vibration ceramic capable of ultrasonic vibration. The oscillator 32 may have one surface that is a positive electrode plate and the other surface that is a negative electrode plate.

A thickness of the oscillator 32 may be about 5 mm or less.

The oscillator 32 may be disposed between the conductive adhesive 66 of the positive electrode substrate 40 and the conductive adhesive 66 of the negative electrode substrate 50 and may be in surface contact with one surface of the conductive adhesive 66 of the positive electrode substrate 40 and one surface of the conductive adhesive 66 of the negative electrode substrate 50.

The oscillator 32 may be provided in plurality, and the plurality of oscillators may be disposed between the conductive adhesive 66 of the positive electrode substrate 40 and the conductive adhesive 66 of the negative electrode substrate 50.

When the plurality of ultrasonic vibrators 30 are disposed to be spaced apart from each other, the conductive sheet 64 may include a conductive sheet portion 67 and a bridge 68.

The conductive sheet portion 67 may be disposed between the conductive adhesive 66 and the insulating film 62.

The conductive sheet portion 67 may be provided in plurality. The conductive sheet portion 67 may have a circular shape. The plurality of conductive sheet portions 67 may be spaced apart from each other.

The same number of ultrasonic vibrators 30 may be provided in the conductive sheet portions 67 of each of the positive electrode substrate 40 and the negative electrode substrate 50.

The same number of insulating films 62 and conductive adhesive 66 as the ultrasonic vibrator 30 may be provided on each of the positive electrode substrate 40 and the negative electrode substrate 50.

The bridge 68 may connect a pair of conductive sheet portions 67 among the plurality of conductive sheet portions to each other.

The bridge 68 may be provided in plurality. The bridge 68 may have a shape that is capable of being bent well, and each of the plurality of bridges 68 may have a zigzag shape. The plurality of bridges 68 may be bent so that adjacent ultrasonic vibrators are inclined at a predetermined angle with respect to each other.

The bridge 68 may have the zigzag shape in which a band having a predetermined width Y is formed. The bridge 68 may have the width Y that is less than a diameter X of the conductive sheet portion 67.

The bridge 68 includes a plurality of unit bridges **68*a* disposed between the conductive sheet portions 67 and spaced apart from each other in a spaced direction of the conductive sheet portion 67, and a return bridge 68*b* connecting a pair of adjacent unit bridges 68*a* of the plurality of unit bridges 68*a*** to each other.

A distance Z between the pair of unit bridges **68*a* may be less than the diameter X of the conductive sheet portion 67. The distance Z between the pair of unit bridges 68*a* may be greater than the width Y of the bridge 68**.

Each of the positive electrode substrate 40 and the negative electrode substrate 50 may include an insulating body 69 (insulation layer) attached to the plurality of bridges 68. The insulating body 69 may be adhesive. The insulating body 69 may include a PI layer.

The insulating body 69 may be disposed on each of the bridges 68 of the positive electrode substrate 40 and the negative electrode substrate 50, on surfaces facing the bridges of the other substrates facing each other.

The insulating body 69 may be disposed on a surface of the negative electrode substrate 50, which faces the bridge 68, on the bridge 68 of the positive electrode substrate 40.

In addition, the insulating body 69 may be disposed on a surface of the positive electrode substrate 40, which faces the bridge 68, on the bridge 68 of the negative electrode substrate 50.

The insulating body 69 of the positive electrode substrate 40 and the insulating body 69 of the negative electrode substrate 50 are spaced apart from each other in a thickness direction of the wearable device.

In each of the positive electrode substrate 40 and the negative electrode substrate 50, the bridge 68 of the conductive sheet 64 may be insulated by an insulating body 69, and the positive electrode substrate 40 and the negative electrode substrate 50 may be maintained so as not be in contact with each other.

FIG. 4 is an enlarged view of an inner protrusion according to an embodiment of the present invention.

The inner body 2 may have a plurality of protrusions 6 protruding from an outer surface.

The plurality of protrusions 6 may include a pillar 7 protruding from the inner body and a head 8 protruding from an end of the pillar 7.

A length L of each of the plurality of protrusions 6 may be about 50 μm to about 1,000 μm.

A diameter D of the head 8 may be about 50 μm to about 300 μm.

In the plurality of protrusions 6, an interval G between the heads 8 may be about 50 μm to about 1,000 μm.

The plurality of protrusions 6 may be a gecko-inspired adhesive having a fine ciliary structure similar to a shape of a sole of a Gecko *japonicus* and may be attached and detached harmlessly to the user's body without a separate adhesive component.

Since the wearable device of the present embodiment operates while being attached to the user's body, both hands of the user are free and may be freely used anytime and anywhere without restrictions on the user's activity.

The plurality of protrusions 6 may protrude in various structural shapes such as circular, hexagonal, and triangular shapes.

FIG. 5 is a cross-sectional view illustrating another example of the wearable device according to an embodiment of the present invention.

The ultrasonic vibrator 30 includes the oscillator 32 and a frequency correction member 34 disposed between the oscillator 32 and the positive electrode substrate 40.

The frequency correction member 34 may be made of aluminum. When the frequency correction member 34 made of aluminum is attached to the oscillator 32, a resonant frequency band may be corrected.

The ultrasonic vibrator 30 may include an inner adhesive member 36 disposed between the oscillator 32 and the frequency correction member 34.

The inner adhesive member 36 may be a mixture of conductive epoxy and AL.

FIG. 6 is a view illustrating an example in which the wearable device is a band attached to a wrist according to an embodiment of the present invention, FIG. 7 is a view illustrating an example in which the wearable device is a patch attached to a face according to an embodiment of the present invention, and FIG. 8 is a view illustrating an example in which the wearable device is a mask according to an embodiment of the present invention.

An example of the wearable device may be a band B wound around the user's hand, as illustrated in FIG. 7.

An example of the wearable device may be a patch P to which a user's face is attached, as illustrated in FIG. 7.

An example of the wearable device may be a face mask M that is capable of covering the user's face, as illustrated in FIG. 8.

In the case of the band B or the face mask attached to the user's body, the wearable device may be about 5 mm or less and may be about 0.1 mm or more.

The ultrasonic generator 20 constituting the wearable device may include the plurality of oscillators and may be the film-type ultrasonic generator (or the flexible ultrasonic generator) in which the bridge 69 is capable of being bent or curved along the curved surface of the body.

In the wearable device, the film-type ultrasonic generator constituted by the plurality of oscillators supplies energy of about 20 kHz to about 10 MHz to the user's body (body or face) to help active ingredients of cosmetics so as to be optimally absorbed.

The film-type ultrasonic generator may apply ultrasonic waves together with various energy sources (e.g., LED, OLED, microcurrent, vibration, heat, etc.), and in this case, efficacy of skin care or body care may be further improved.

FIG. 9 is a view illustrating performance of the wearable device according to an embodiment of the present invention.

The film-type ultrasonic generator 20 may be adjusted in a frequency range of about 20 kHz to about 10 MHz, and an output intensity may be controllable in in output intensity range of about 30 $mW/cm^2$ to about 550 $mW/cm^2$. Here, a turn-on time may be adjusted in a range of about 2 minutes to 30 minutes.

The film-type ultrasonic generator 20 may control an ultrasonic energy supply time by adjusting a duty ratio (%) of a modulation clock, based on the modulation clock.

The duty ratio (%) may be set according to the range of about 5 Hz to about 100 Hz for the modulation clock, and thus, an ultrasonic energy supply time is energy-controlled into a pulse length.

As an example, the resonance frequency may be about 320 kHz, the modulation clock may be about 10 Hz, and the duty ratio may be about 60% to about 90%.

After the active ingredient (functional cosmetic) is applied to the user's face, an example, in which the wearable device is worn, may be also possible, and before applying the active ingredient (functional cosmetic) to the user's face, an example, in which the wearable device is worn, and the active ingredient (functional cosmetics) is applied may also be possible.

FIG. 9 illustrates results obtained by comparing skin permeability when applying ultrasonic waves having about 320 kHz after applying niacinamide to a pig skin when compared to Comparative Example.

Comparative Example is a case in which niacinamide is applied to the pig skin, and the ultrasonic waves are not applied.

Embodiment 1 is a case in which niacinamide is applied to the pig skin, and the ultrasonic waves are applied at a duty ratio of about 60% for the application time of about 4 minutes.

Embodiment 2 is a case in which niacinamide is applied to the pig skin, and the ultrasonic waves are applied at a duty ratio of about 90% for the application time of about 4 minutes.

Embodiment 3 is a case in which niacinamide is applied to the pig skin, and the ultrasonic waves are applied at a duty ratio of about 60% for the application time of about 4 minutes.

Embodiment 4 is a case in which niacinamide is applied to the pig skin, and the ultrasonic waves are applied at a duty ratio of about 90% for the application time of about 4 minutes.

The relative skin permeability (%) of this embodiment based on the skin permeability of about 100% according to Comparative Example may be approximately 287% to approximately 346%, and it may be confirmed that the skin permeability is significantly higher than that of the Comparative Example.

The above-disclosed subject matter is to be considered illustrative, and not restrictive, and the appended claims are intended to cover all such modifications, enhancements, and other embodiments, which fall within the true spirit and scope of the present invention.

Thus, the embodiment of the present invention is to be considered illustrative, and not restrictive, and the technical spirit of the present invention is not limited to the foregoing embodiment.

Therefore, the scope of the present invention is defined not by the detailed description of the invention but by the appended claims, and all differences within the scope will be construed as being included in the present invention.

The invention claimed is:

1. A wearable device, comprising:
an inner body;
an ultrasonic generator coupled to the inner body;
an outer body coupled to the ultrasonic generator,
wherein the ultrasonic generator comprises:
at least one ultrasonic vibrator;
a positive electrode substrate connected to the at least one ultrasonic vibrator; and
a negative electrode substrate connected to the at least one ultrasonic vibrator,
wherein the at least one ultrasonic vibrator is disposed between the positive electrode substrate and the negative electrode substrate, and
at least one of the positive electrode substrate or the negative electrode substrate comprises:
an insulating film; and
a conductive sheet coupled to the insulating film, and
a conductive adhesive disposed between the conductive sheet and the ultrasonic vibrator, wherein the conductive sheet further comprises:

a plurality of conductive sheet portions disposed between the conductive adhesive and the insulating film; and a plurality of bridges, each configured to connect a pair of conductive sheet portions of the plurality of conductive sheet portions to each other, wherein the wearable device further comprises:

an insulating body disposed on surfaces of the plurality of bridges of the positive electrode substrate and on surfaces of the plurality of bridges of the negative electrode substrate, wherein the surfaces of the plurality of bridges of the positive electrode substrate face the surfaces of the plurality of bridges of the negative electrode substrate.

2. The wearable device according to claim 1, wherein the ultrasonic generator further comprises:

a plurality of ultrasonic vibrators disposed between the positive electrode substrate and the negative electrode substrate, wherein the plurality of ultrasonic vibrators are connected to the positive electrode substrate and the negative electrode substrate, and wherein the plurality of ultrasonic vibrators are spaced apart from each other.

3. The wearable device according to claim 2, wherein the plurality of ultrasonic vibrators are spaced at an interval of about 5 mm or more from each other.

4. The wearable device according to claim 2, wherein each of the plurality of bridges is shaped to form a zigzag shape.

5. The wearable device according to claim 1, wherein the insulating film comprises polyimide (PI) material, the conductive sheet comprises copper material, and the conductive adhesive comprises a conductive double-sided tape.

6. The wearable device according to claim 5, wherein at least one of the inner body or the outer body comprise silicon.

7. The wearable device according to claim 1, wherein the at least one ultrasonic vibrator further comprises:

an oscillator; and a frequency correction member disposed between the oscillator and the positive electrode substrate.

8. The wearable device according to claim 7, wherein the frequency correction member comprises an aluminum material.

9. The wearable device according to claim 7, further comprising an inner adhesive member disposed between the oscillator and the frequency correction member.

10. The wearable device according to claim 9, wherein the inner adhesive member comprises a mixture of conductive epoxy and AL.

11. The wearable device according to claim 1, wherein the positive electrode substrate is coupled to the inner body.

12. The wearable device according to claim 1, wherein at least a portion of the positive electrode substrate is disposed between the at least one ultrasonic vibrator and the inner body.

13. The wearable device according to claim 1, wherein an outer surface of the inner body is shaped to include a plurality of protrusions that protrude from the inner body.

14. The wearable device according to claim 13, wherein each of the plurality of protrusions comprises:

a pillar protruding from the inner body; and a head protruding from an end of the pillar.

15. The wearable device according to claim 14, wherein each of the plurality of protrusions has a length of about 50 μm to about 1,000 μm, and the head, for each of the plurality of protrusions, has a diameter of about 50 μm to about 300 μm.

16. The wearable device according to claim 14, wherein a distance between the head, for each of the plurality of protrusions, ranges from about 50 μm to about 1,000 μm.

* * * * *